(12) United States Patent
Heiser

(10) Patent No.: US 8,246,348 B2
(45) Date of Patent: *Aug. 21, 2012

(54) SELF-LIGATING ORTHODONTIC BRACKET

(76) Inventor: Wolfgang Heiser, Innsbruck (AU)

( * ) Notice: Subject to any disclaimer, the term of this patent is extended or adjusted under 35 U.S.C. 154(b) by 98 days.

This patent is subject to a terminal disclaimer.

(21) Appl. No.: 12/828,917

(22) Filed: Jul. 1, 2010

(65) Prior Publication Data

US 2010/0285421 A1    Nov. 11, 2010

Related U.S. Application Data

(63) Continuation-in-part of application No. 12/343,593, filed on Dec. 24, 2008, now Pat. No. 7,967,603.

(30) Foreign Application Priority Data

Dec. 27, 2007  (DE) .......................... 10 2007 062 735
Jul. 2, 2009   (DE) .......................... 10 2009 031 495

(51) Int. Cl.
    *A61C 7/12* (2006.01)
(52) U.S. Cl. ........................................................ 433/10
(58) Field of Classification Search .................. 433/8, 9, 433/10, 11, 13, 14
    See application file for complete search history.

(56) References Cited

U.S. PATENT DOCUMENTS

| | | | |
|---|---|---|---|
| 4,634,662 A | 1/1987 | Rosenberg | |
| 4,712,999 A | 12/1987 | Rosenberg | |
| 5,474,445 A | 12/1995 | Voudouris | |
| 5,562,444 A | 10/1996 | Heiser et al. | |
| 5,685,711 A | 11/1997 | Hanson | |
| 6,776,613 B2 | 8/2004 | Orikasa | |
| 6,942,483 B2 | 9/2005 | Heiser | |
| 7,967,603 B2 * | 6/2011 | Heiser | 433/10 |
| 2006/0110699 A1 | 5/2006 | Forster | |
| 2007/0072143 A1 | 3/2007 | Sommer | |

FOREIGN PATENT DOCUMENTS

EP    1452148 A2    2/2004

* cited by examiner

*Primary Examiner* — Ralph Lewis
(74) *Attorney, Agent, or Firm* — Jansson Shupe & Munger Ltd.

(57) ABSTRACT

A self-ligating orthodontic bracket with a replaceable closing spring member detachably connected to the upper structure of a tooth-attachable base member. Particular preferred embodiments relate to the form of detachable connection of the closing spring member with the upper structure, with one particularly preferred embodiment being torsion tabs that are reversibly deformable to maintain pivoting engagement of spring member and upper structure when desired and easy removal of the spring members when desired.

7 Claims, 16 Drawing Sheets

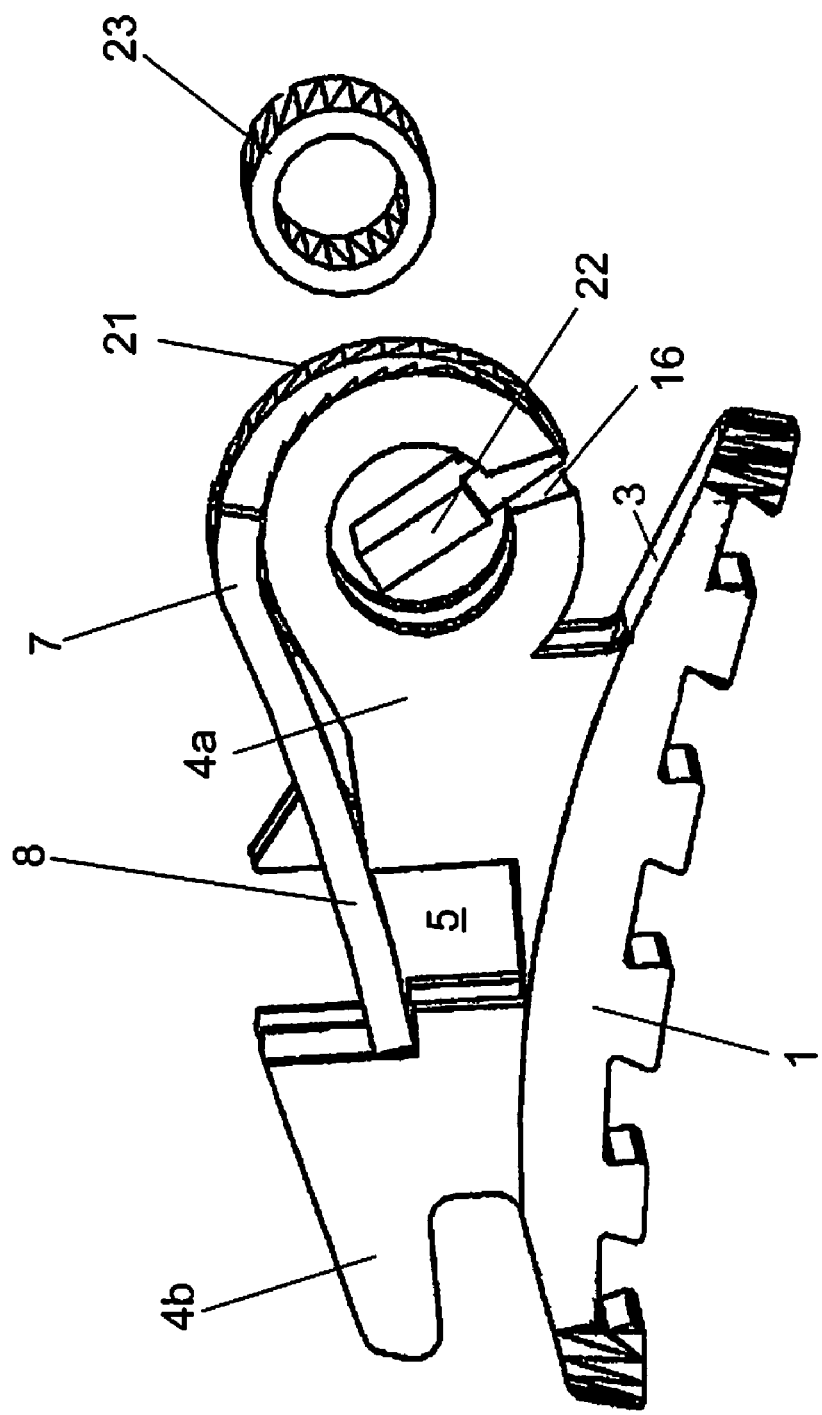

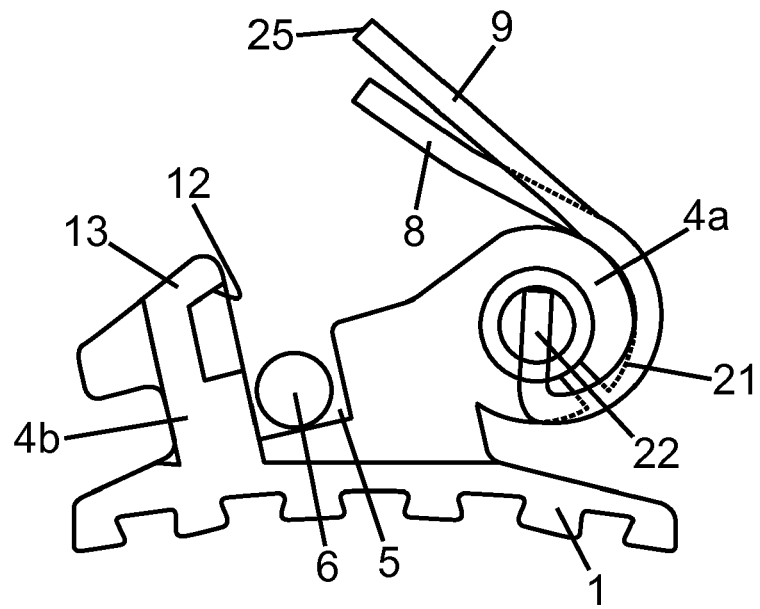
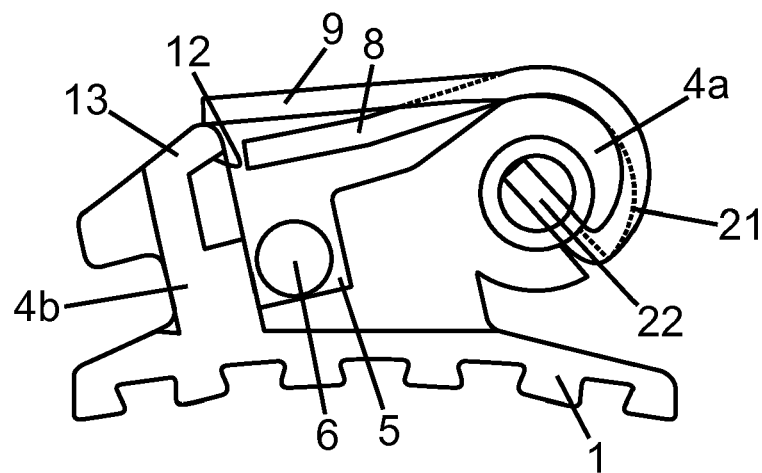
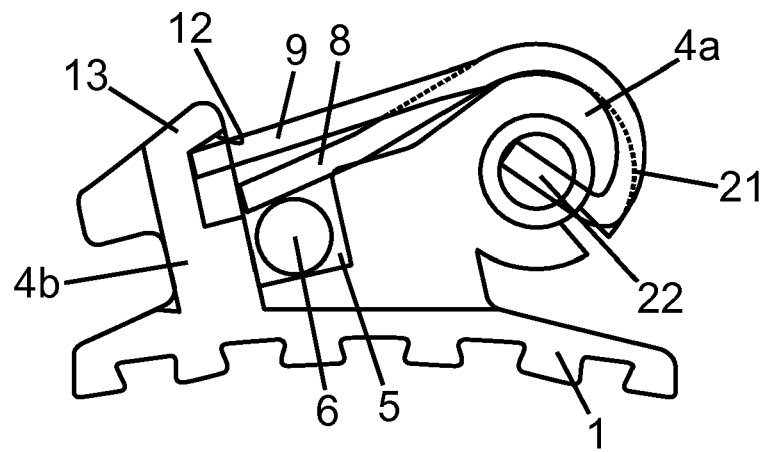

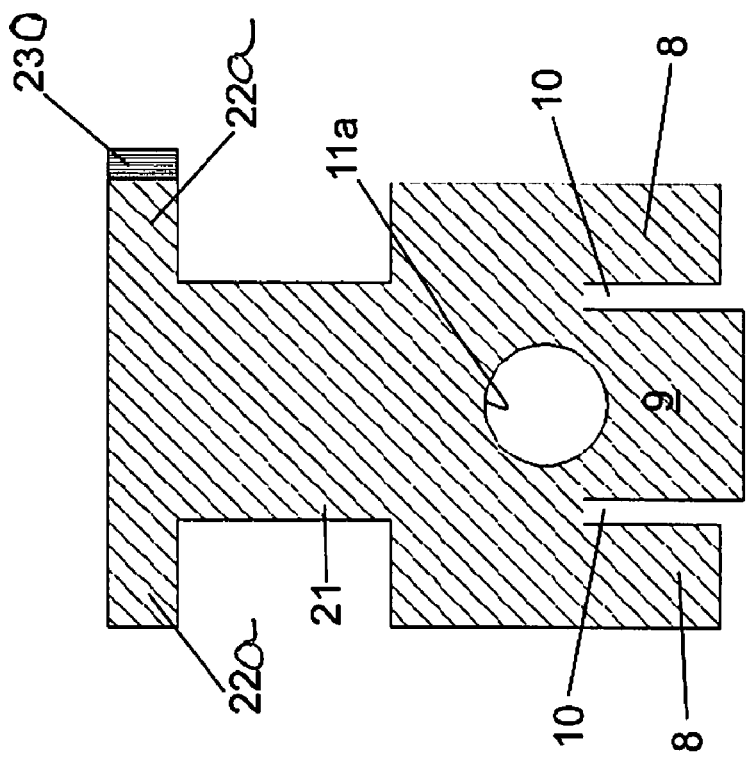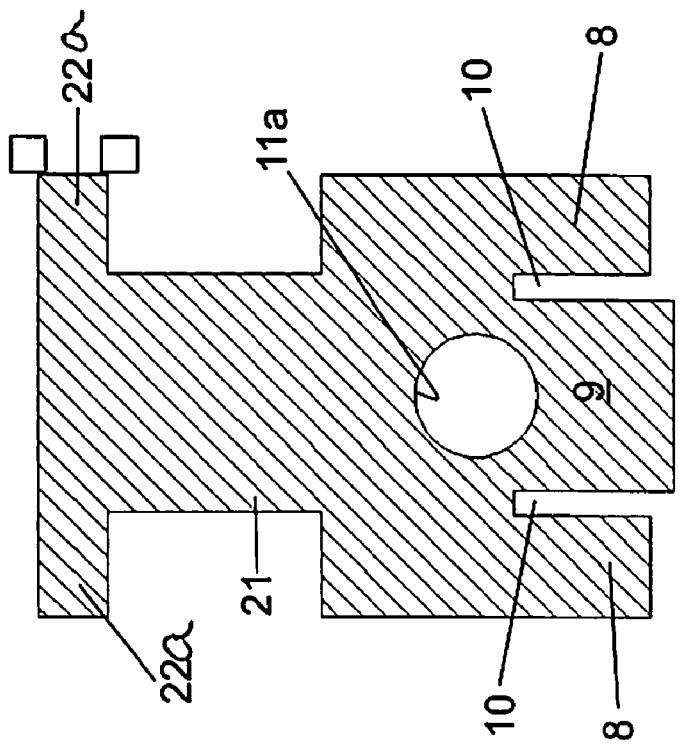

SELF-LIGATING ORTHODONTIC BRACKET

CROSS REFERENCES TO RELATED APPLICATIONS

This application a continuation-in-part of U.S. patent application Ser. No. 12/343,593, filed Dec. 24, 2008, which claims priority based on German patent application DE 10 2007 062 735.3, filed Dec. 27, 2007. This application also claims priority on German patent application DE 10 2009 031 495, filed Jul. 2, 2009.

FIELD OF THE INVENTION

The invention disclosed herein pertain to self-ligating orthodontic brackets of the type including a (1) base member with a tooth-securable bottom side and a top side from which upper structure extends, the upper structure having first and second tie wings defining an arch-wire-receiving slot therebetween and forming at least one undercut on the second tie wing, and (2) a closing spring member with a first end pivotably anchored to the first tie wing and a second end that is releasably engageable with the undercut(s) on the second tie wing and has at least one ligating tongue covering the arch wire. The inventive structures are improvements in such devices.

BACKGROUND OF THE INVENTION

Orthodontic brackets of the type to which this invention pertains are cemented by their base plates to the teeth of the row to be corrected, and the arch wire is inserted through the slots of all of the brackets attached to the row of teeth and are secured in position there by a ligature tongue which extends across the arch wire lying in the slot. In such devices, the closing spring member is movable between an open position allowing insertion of the arch wire into the slot and a closed position in which the at least one ligating tongue covers the arch wire. U.S. Pat. No. 6,942,483 is an example of this class of products.

Prior to the introduction of orthodontic brackets using such closing spring members with their ligating tongues, rings of elastic material were wrapped around tie wings formed on the upper structures. The use of closing spring members in place of elastic rings has facilitated changing of the arch wire, which must be done several times during the course of an orthodontic treatment. This has made such changing steps less time-consuming.

The interacting structures (i.e., closing spring member and base member) of the type of orthodontic brackets of which the invention herein is an improvement are now further described. The second end of the closing spring member is formed by tongues. At least one of such tongues is a latching tongue that is releasably engageable with an undercut of the second tie wing of the base-member upper structure, and at least one other of the tongues is a ligating tongue, which extends transversely across the arch-wire-receiving and, as noted above, covers the arch wire. The tongues forming the second end of the closing spring member are separated from each other by notches. The closing spring members are made of spring steel sheet and are stamped out.

One self-ligating orthodontic bracket of the prior art is, as mentioned above, that disclosed in U.S. Pat. No. 6,942,483. This device has a closing spring consisting of a spring steel sheet member which is permanently attached to the upper bracket structure. The spring member includes a latching tongue which is stamped out between two parallel ligating tongues. The latching tongue is bent essentially at a right angle to the ligating tongues and is bent again at its free end so that it can engage underneath a retaining projection formed on the upper bracket structure when the spring member is in the securing position—i.e., the position in which the ligating tongues extend transversely across the slot and the arch wire therein.

Another self-ligating orthodontic bracket of the prior art is known from U.S. Pat. No. 5,685,711. In such device, the closing spring consists of a ligating arm extending across the slot and a locking arm extending over and essentially parallel to the ligating arm. The two arms are connected to each other by a connecting section, which is bent into a circle and which cooperates with pins formed on the upper bracket structure to form a hinge. The closing spring can pivot between an open position, which makes the slot freely accessible, and a closed position. During production of such orthodontic bracket, the upper structure of the bracket is assembled from two halves which are essentially mirror images of each other, and the closing spring is inserted when the two halves are being assembled. Given that the two halves of the upper bracket structure are then welded together, it is impossible to replace the closing spring if it becomes damaged.

Still another self-ligating orthodontic bracket of the prior art is seen in U.S. Pat. No. 5,562,444. Such prior art bracket has a movable but captured closing spring, the closing spring being formed without a fork and being held immovably and undeformably only by its intrinsic elastic force in the opened or closed positions. More specifically, the force which the closing spring exerts on the arch wire is determined only by the type of material selected for the closing spring, and therefore cannot be adjusted. Such prior art patent also discloses projections on the second bracket tie wing, under which, in the closed position, the terminal edge of the closing spring lies so that the spring cannot be opened unintentionally. These projections are not able to produce any pre-tension in the closing spring.

It would be desirable to have closing spring members which are not essentially permanently attached to the orthodontic bracket base member, because permanent attachment makes it impossible to replace the closing springs if they become damaged. It would also be desirable for the closing spring members of such self-ligating brackets to be well secured in their closed position to prevent them from opening unintentionally. And, it would also be highly desirable that a closing spring member which is replaceable (because not permanently attached to the bracket base member) would be configured such that, when inserted into the bracket base member but still in the open position, would not fall out of its engagement with the bracket base member.

OBJECTS OF THE INVENTION

One object of the present invention is to provide an self-ligating orthodontic bracket with a replaceable closing spring.

Another object of the invention is to provide a replaceable closing spring for such orthodontic brackets which can be produced by means of a simple stamping and bending process.

Another object is to provide an orthodontic bracket with a closing spring member which can be easily pivoted.

Another important object of the invention is to provide a self-ligating orthodontic bracket having a replaceable spring closing member which is readily prevented from falling out of its engagement with the base member, but also released from its engagement with the base member in a simple manner by the use of a conventional tool without the need for any additional locking elements.

SUMMARY OF THE INVENTION

In one embodiment of the invention, the latching tongue, which holds the closing spring, is between two ligating tongues but, in contrast to one prior art device, is relatively short and is not bent out of the plane which defines the ligating tongues. Instead, the latching tongue extends between the ligating tongues to a free end in substantially the same plane as the plane of the ligating tongues. In the closed position of the spring, the free end of the latching tongue fits under a projection formed on the upper bracket structure; the cooperation between the latching tongue and this projection prevents the closing spring from being opened unintentionally. If it is desired to open the closing spring, it is sufficient to simply use a needle-like tool to disengage the latching tongue from the latching projection. It is especially effective for the latching projection to be divided in the middle by a gap extending transversely to the direction in which the wire-receiving slot extends, so that the free end of the latching tongue is accessible to the needle-like tool, with the result that the latching tongue can be pushed transversely to the slot and thus disconnected from its locking engagement.

The force applied to the latching tongue by the tool between the ligating tongues makes it possible for the latching tongue to be pushed elastically out of engagement with the latching projection of the upper bracket structure.

In another embodiment of the invention, a single ligating tongue is present between two latching tongues. In this embodiment, when the closing spring is in the closed position the tongues extend across the arch-wire-receiving slot. The free ends of the latching tongues engage in undercuts which are formed on the upper bracket structure.

In both embodiments, when the closing spring is in the closed position the ligating tongue(s) are pre-tensioned in the direction toward the arch-wire-receiving slot (possibly to different degrees) so that a force can be exerted on the arch wire present in the slot, namely, a force which makes it possible to use the bracket as a so-called "active" bracket, in which the closing spring not only secures the arch wire in its slot but also can actively produce a torque toward the arch-wire slot and, depending on the arch wire position, on the arch wire itself.

The spring can be anchored on the upper bracket structure in the same manner as that described in the prior '444 and '484 patents. The present invention can be realized in an especially advantageous manner in combination with an attachment method in which the anchoring end of the closing spring forms part of a hinge, because, as a result, the arc between the tongues and the anchoring point becomes comparatively short. In turn the elastic restoring forces, which keep the spring in its closed position, become stronger. According to the invention, a bore extending parallel to the wire slot is formed in the bracket tie wing around which the arc (curved wrap-around portion) of the closing spring is wrapped. The tie wing has a gap extending transversely to the wire-receiving slot. The gap divides the tie wing into two halves a certain distance apart and into which the arc-like (curved) section of reduced width of the closing spring extends. This arc-like section is provided on each side of its free end with a tab, and each tab can be inserted into one of the bores in the bracket tie wing.

To avoid the upper bracket structure having to be produced as two separate parts to allow the mounting of the spring, as in the case of the bracket according to the prior '711 patent, the bore in one of the two halves of the tie wing has a radially oriented feed slot. In the assembled state of the spring, this feed slot may closed off by a bearing bush, which is introduced into the bore and surrounds the tab of the closing spring that is present there.

This way of supporting the closing spring is independent of the way in which the closing spring is secured in its closed position, but it can be applied to advantageous effect in the case of the inventive bracket.

Certain other highly preferred embodiments include improvements which change the nature of the engagement of the tabs of the spring closing member with the bores in the tie wing of the upper structure. This highly preferred embodiment overcomes some disadvantages of the embodiment which includes a bearing bush, by eliminating the significant effort that may be required to remove the bearing bush (from the bore in which it is inserted) in order allow release the tab. This highly preferred embodiment, which as will be seen has the further advantage of eliminating a component (namely, the bearing bush), is now described in further detail.

The closing spring includes, at its first end, what will be referred to herein as a "torsion tab." The torsion tab can be introduced into the aforementioned feed slot and the shape of the torsion tab in the bore can be changed by twisting its end in such a way that the closing spring cannot be removed and cannot fall out until the torsion tab is twisted back into its original position. Twisting the torsion tab away from its original position (and shape) effectively prevents the closing spring from being removed through the feed slot. As a result, it is possible for an orthodontist to introduce the closing spring easily into the bracket and, by simply twisting the torsion tab, to secure it against falling out unintentionally. Thus the need for any additional components of the spring or the bracket body is eliminated.

The shape of the torsion tab is usually changed by twisting the reversible material. The material is "reversible" in the sense that its original shape can be restored after deformation by twisting the tab as appropriate in the opposite direction, where it will stay in its restored shape. In one form, the torsion tab can include a bearing of such a kind that the free end of the torsion tab can be twisted around the axis of the bore with respect to the other end of the torsion tab. The bearing mechanism can be designed, for example, as a ball bearing or similar suitable type of bearing, wherein the function of the twisting of the free end of the torsion tab with respect to the adjoining body of the tab is the essential point.

Twisting of the torsion tab is possible with the help of a tool such as a pair of pliers and is carried out in such a way that it is impossible, or at least extremely difficult, for the tab to turn by itself or for someone to turn it back (e.g., only with fingers, without placing a tool on it).

The end of the torsion tab of the closing spring is preferably flush with the bore on the outside. It can also be shorter or even somewhat longer; i.e., it can project out from the bore. This can facilitate easy gripping, e.g., with pliers The angle by which the torsion tab can be twisted is advantageously between about 5° and 60°, and preferably between about 10° and 30°. The amount of twist used should give a high degree of certainty that wiggling or turning of the closing spring will not cause the torsion tab to slip out through the feed slot. Of course, the torsion tab should not be deformed in a way that would prevent the closing spring from rotating in hinge-like fashion around the center axis of the bore.

It is especially advantageous for the inventive bracket to be designed as a passive bracket, wherein the retaining elements on the second end of the closing spring hold the arch wire in the slot. A "passive bracket" in the present context is understood to be a bracket in which the arch wire is held in the slot with precisely defined retaining forces so that it can exert a certain force in a certain direction on the tooth to be corrected. This force can be changed only by modifying the mounting of the bracket, including the closing spring and the arch wire.

Alternatively, the inventive bracket is designed as an active bracket, wherein the retaining elements formed on the second end of the closing spring secure the arch wire in the slot and can also exert a torque on it simultaneously. In contrast to the above-mentioned passive bracket, the arch wire is not held permanently in a fixed position in the slot of an active bracket; rather, depending on the material properties of the ligating tongues of the closing spring, which also prevent the arch wire from slipping out of the slot, the ligating tongues and the bracket body exert a variable torque on the arch wire. The reason for this is that, although the ligating tongues rest on the arch wire, they are also flexible and can move along with the movement of the arch wire against their material pre-tension.

As already noted, the first wing of the upper structure extending from the base member is preferably divided into two wing half-sections by a notch extending transversely to the slot, with first and second coaxial bores extending through the two half-sections parallel to the slot. The aforementioned feed slot providing access for tab entry into the bore extends toward the top surface of the base plate from the first bore in one of the two half-sections, and the closing spring, at its first end, includes an additional tab lying opposite the torsion tab, this additional tab being held in the second bore. The second bore comprises an additional feed slot parallel to the feed slot of the first bore, and the additional tab is also designed as a torsion tab.

Because of such doubling of the mechanism for securing and holding the closing spring, the inventive bracket can be used in different ways, given that the securing of the closing spring in place needs to be done only on one of the two sides. Where suitable geometric limitations are present because of the particular orthodontic treatment situation involved, it is also possible to introduce and to secure the closing spring in place by twisting the torsion tabs on both sides.

It is also advantageous for the closing spring to include a recess so that it can be opened or closed with a tool. The recess can be a complete circular hole in the closing spring, but it can also be a recess at the edge of the closing spring, designed in such a way that a tool can exert a lifting force capable of opening or closing the previously inserted and secured closing spring.

BRIEF DESCRIPTION OF THE DRAWINGS

FIG. 4 is a side view of the bracket of FIG. 1 with the spring in its closed position, without the arch wire and with a separately illustrated bearing bush.

FIGS. 5a-5c illustrate the bracket of FIG. 1 from the side with the closing spring in different positions.

FIGS. 8a-8c are side views of a second embodiment of the invention similar to the views of FIGS. 5a-5c, with the closing spring in different positions.

FIGS. 15a and 15b are developed views of two embodiments of the closing springs.

DETAILED DESCRIPTION OF PREFERRED EMBODIMENTS

Figure 1:
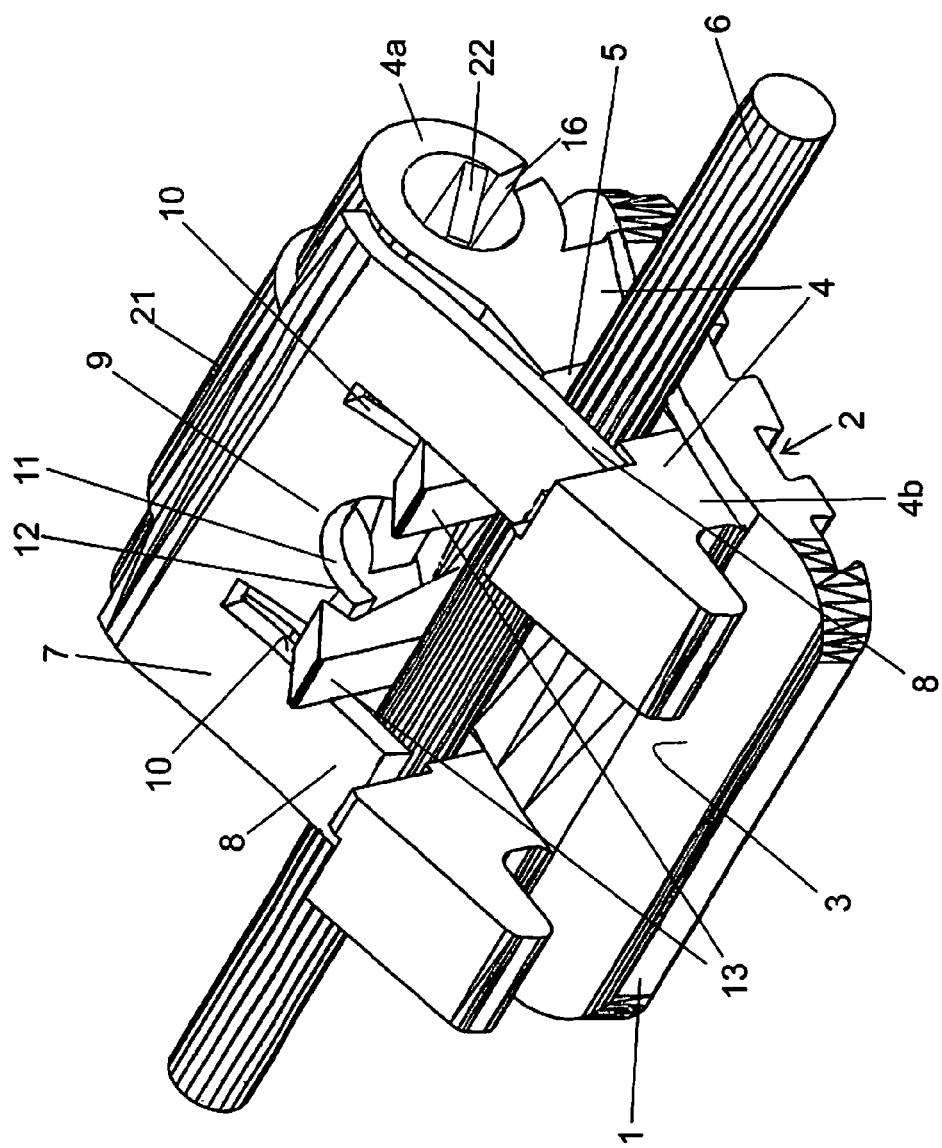
FIG. 1 is perspective view of a first embodiment of an inventive bracket with an arch wire inserted therein.

The figures illustrate various preferred embodiments of orthodontic brackets in accordance with this invention. Common or similar parts are given the same numbers in the drawings of all embodiments.

FIG. 1 shows a first embodiment of the inventive self-ligating orthodontic bracket in its entirety with a closing spring in the closed and secured state and with an arch wire held by the spring. The bracket has a base plate 1, which includes a bottom surface 2, designed to be fastened to a tooth, and a top surface 3. An upper structure, designated overall by the number 4, rises from top surface 3. Upper structure 4 includes a first wing 4a and a second wing 4b. A slot 5 extends between wings 4a and 4b. An arch wire 6, which is not part of the bracket, is held in slot 5. Wings 4a and 4b have a gap transverse to the longitudinal dimension of slot 5; this gap divides each of the two wings into two half-sections, which are spaced a certain distance apart.

A closing spring, designated overall by the number 7, preferably made of high-grade spring steel (although other materials, e.g., other metals, metal alloys, or even plastic, can also be used), is also part of the bracket. Closing spring 7 has a first end with two tabs 22 which are anchored on the first wing 4a of the bracket upper structure 4 in ways to be described later. Closing spring 7 has also a central section 21 of reduced width. Closing spring 7 also has a second end which is formed by three tongues, namely, two parallel ligating tongues 8 which extend transversely over slot 5 and arch wire 6 present therein, and a locking tongue 9 which extends between ligating tongues 8 and is separated from ligating tongues 8 by two notches 10 in the spring plate.

The locking tongue 9 is short enough that it does not extend over slot 5. At its free end (edge) close to slot 5, locking tongue 9 has a semicircular recess 11 to accept a pin-like tool. In the closed position of closing spring 7 shown here, the free edge of locking tongue 9 is located laterally next to recess 11 and lies under an undercut 12 formed on a projection 13 of upper structure 4. Upper structure 4 also includes a gap extending transversely to wire-holding slot 5, so that the free edge of locking tongue 9, with its recess 11, is accessible to the previously mentioned pin-like tool, which can be introduced between locking tongue 9 and arch wire 5 to push locking tongue 9 away from arch wire 5.

Figure 2:
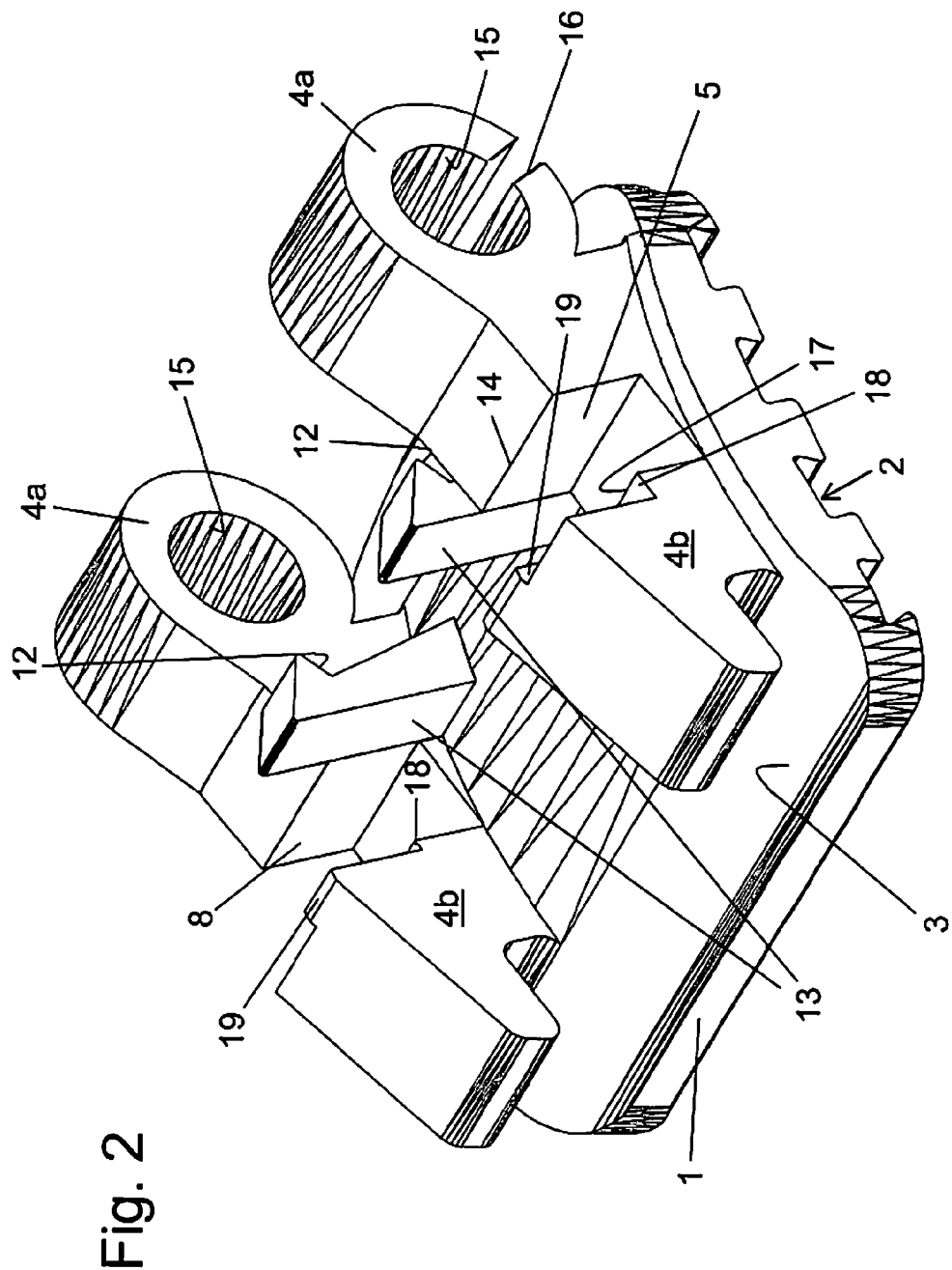
FIG. 2 is a perspective view of the bracket of FIG. 1 without the closing spring.

Reference is now made to FIG. 2 for the explanation of additional details. It can be seen here that undercut 12 on projection 13 is at a level approximately the same as that of upper edge 14 of wire-holding slot 5 on the side of first wing 4a of bracket structure 4. It can also be seen that a bore 15 is formed in first wing 4a, divided by the gap, this bore extending parallel to the longitudinal dimension of slot 5. In one of the two half-sections of first wing 4a, bore 15 has a feed slot 16, which extends radially toward top surface 3 of base plate 1. This feed slot makes it possible to mount closing spring 7 on upper bracket structure 4. For this purpose, closing spring 7 is first inserted in the axial direction into bore 15 of the half-section of first wing 4a without a feed slot 16, and then tab 22 is introduced radially into bore 15 through feed slot 16.

Figure 3:
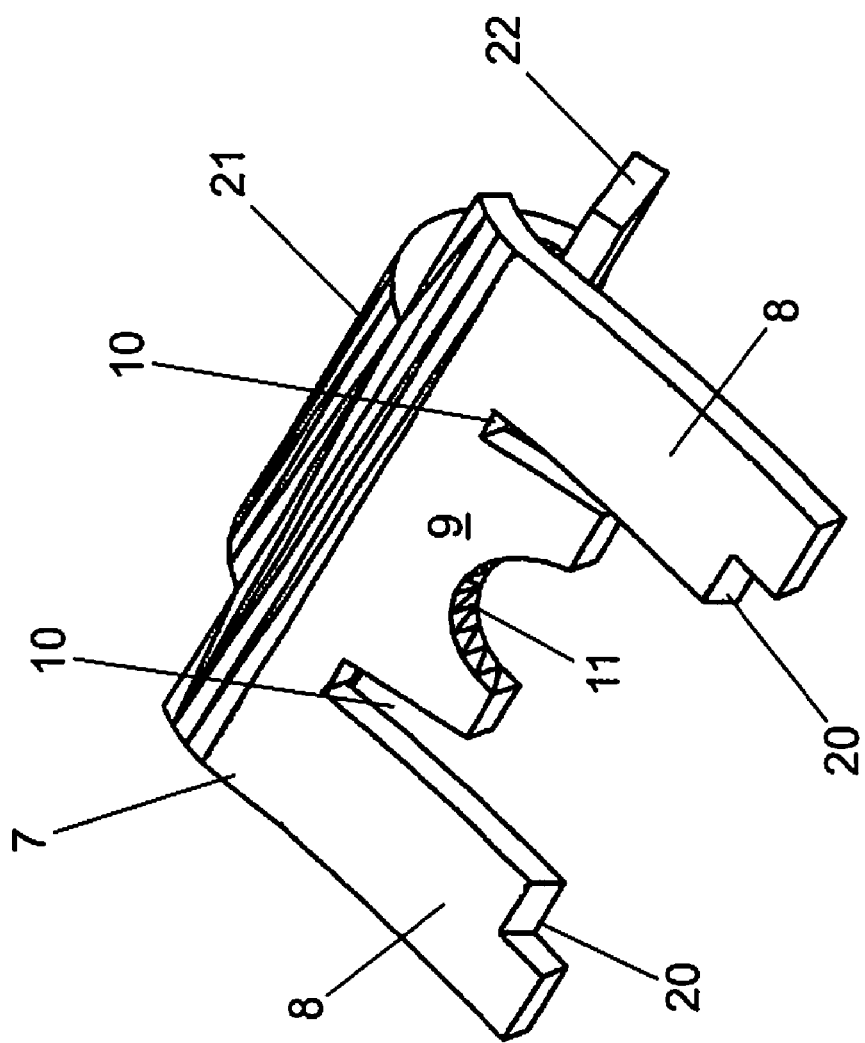
FIG. 3 is a perspective view of the closing spring of the bracket of FIG. 1.

As shown in FIG. 3, closing spring 7 has a cutout 20 at the free end of each of ligating tongues 8. Cutouts 20 cooperate with projections 19 on contact surface 18 to center closing spring 7 and to prevent it from sliding sideways when the free ends of ligating tongues 8 arrive in the closed position and finally rest on contact surfaces 18 of second tie wing 4b (see FIG. 1).

It can be seen in FIG. 3 that an arc (or curved portion) 21, which is of reduced width, adjoins the root area where ligating tongues 8 and interposed latching tongue 9 of closing spring 7 merge with each other. Such structure can be seen in FIGS. 7a and 7b. Adjoining each side of the end of arc 21 of reduced width is tab 22, only one of which can be seen in FIG. 3. The width of the reduced-width area is calculated in such a way that arc-like section 21 of the closing spring can fit between the two halves, created by the gap, of first tie wing 4a.

FIG. 4 shows a side view of the bracket of FIG. 1 in an almost completed state. As can be seen, tab 22 is held in bore 15 in the one half of first tie wing 4a with a certain amount of play. To prevent tab 22 from hooking onto the edges of feed slot 16 when closing spring 7 is opened or closed, a bearing bush 23 is provided, which is pushed, or preferably pressed, into bore 15 to cover feed slot 16 after closing spring 7 has been attached to the bracket. The final assembled state is easily recognized in FIG. 1. So that bore 15 (FIG. 2) can have the same diameter in both halves of first tie wing 4a, tab 22 held by bearing bush 23 is advisably made narrower than the other tab by the amount necessary to avoid a skewed seating of closing spring 7. Such structure is most easily seen in FIGS. 7a and 7b.

Figure 5A:
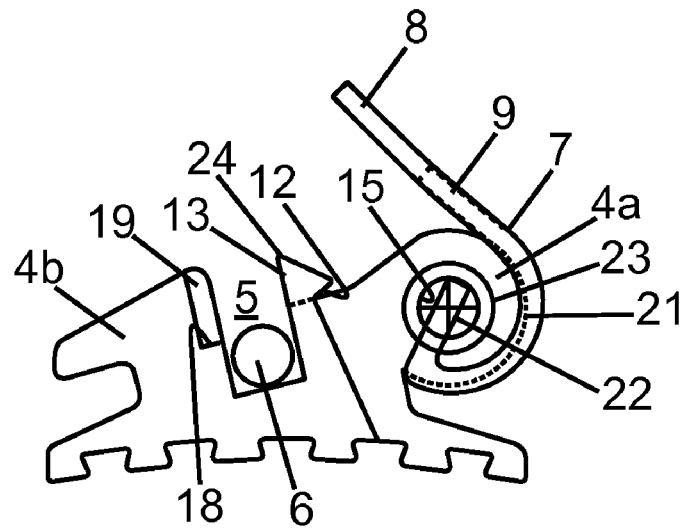
Figure 5B:
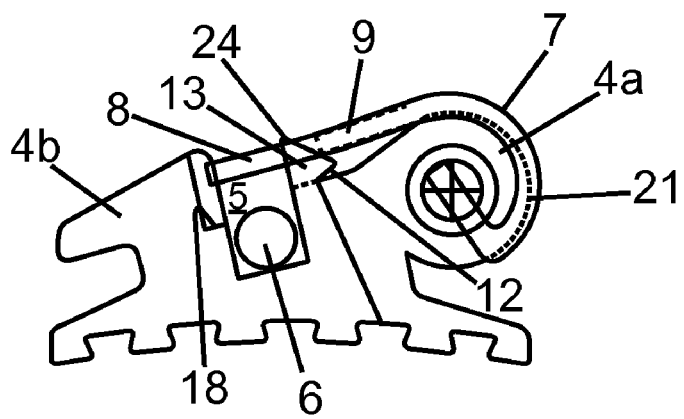
Figure 5B:
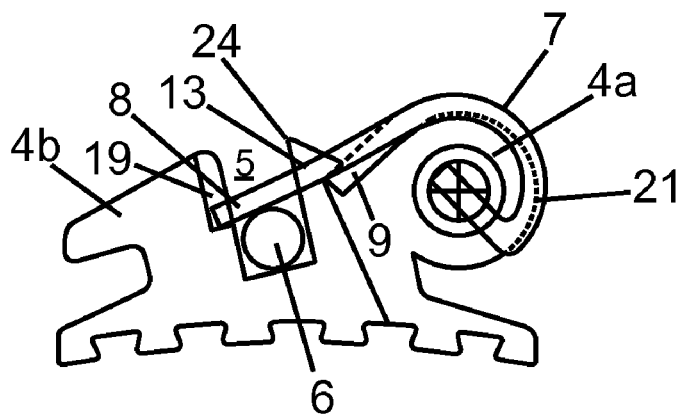

FIG. 5a shows the bracket from the side in the completely opened state of closing spring 7. It can be seen that closing spring 7 has been pivoted around the hinge formed by bore 15 with the help of tabs 22 into the opened, end position. Ligating tongues 8 and latching tongue 9 are relaxed and extend parallel to each other; i.e., they are aligned with each other on the same plane. In FIG. 5b, closing spring 7 has been pivoted into a position in which ligating tongues 8 extend across slot 5 with the arch wire 6 present therein. The free edge of latching tongue 9 rests on a slanted surface 24, which is formed on projection 13.

By pressing further latching tongue 9 from above and possibly also by pressing the spring toward the right in the view according to FIG. 5b, the free edge of latching tongue 9 moves downward over slanted surface 24 until it slides under undercut 12, which is formed on projection 13. This position is shown in FIG. 5c. In this position, closing spring 7 is secured in its closed position. So that enough force can be produced to hold arch wire 6 in position, undercut 12 is located at a level which is approximately the same as that of upper edge 18 of slot 5 in the side of first tie wing 4a. Undercut 12 can be somewhat higher or lower, depending on whether and to what extent latching tongue 9 is bent in the relaxed state with respect to the plane described by ligating tongues 8. To bring latching tongue 9 into the latching position, it must be pushed down. When latching tongue 9 in its latching position, i.e., in the position in which the closing spring is closed, it produces an elastic tension in the closing spring, pressing the ligating tongues downward onto the arch wire. When the free ends of ligating tongues 8 are resting on contact surfaces 18 on the first tie wing (see FIG. 5c), the tongues are bent toward arch wire 6. In order to release closing spring 7 from this position, it is sufficient to simply push latching tongue 9 toward the right until it is free of undercut 12, which is made possible by the elasticity of arch 21, which can escape to the right.

Figure 6A:
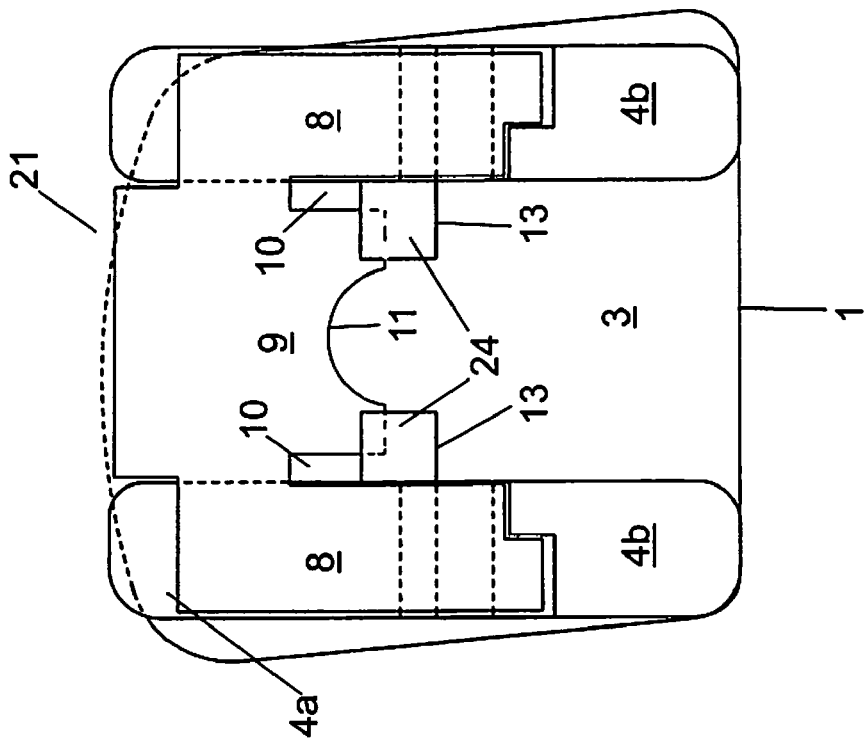
FIGS. 6a and 6b are top views of brackets according to the first embodiment of the invention for use on different teeth.
Figure 6B:
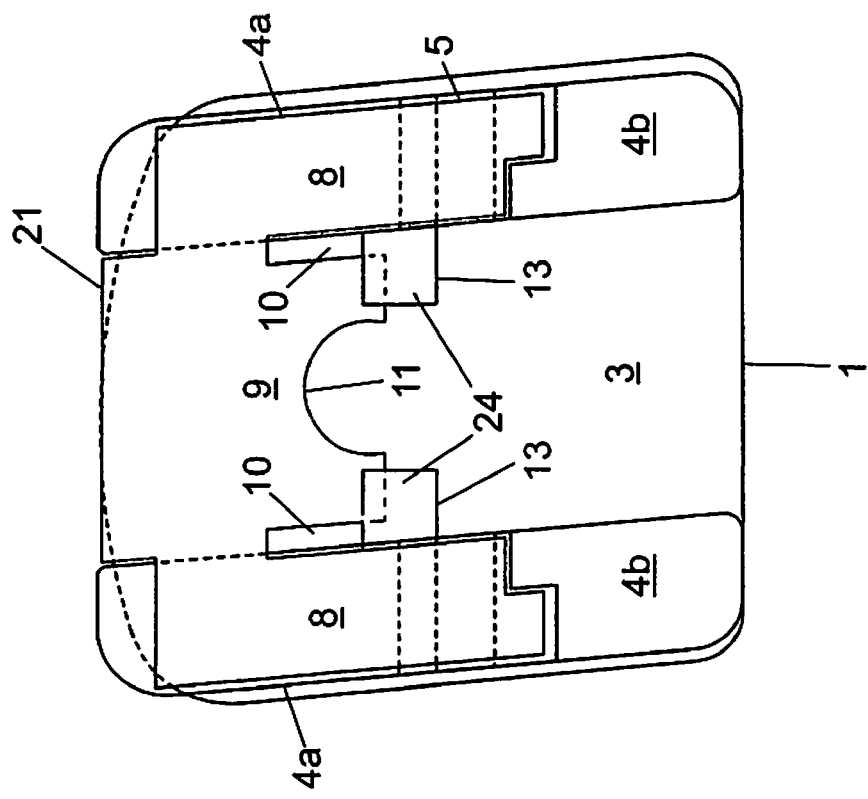

FIGS. 6a and 6b show top views of two embodiments of the inventive brackets for use on different teeth. The embodiment of FIG. 6a differs from that of FIG. 6b in that the upper bracket structure, and correspondingly also the closing spring, have the form of a parallelogram. The embodiment of FIG. 6b is configured generally as a rectangle. These figures are therefore intended to show that the invention can be applied to all bracket configurations, regardless of the location in the row of teeth to be corrected where the bracket is to be used.

Figure 7A:
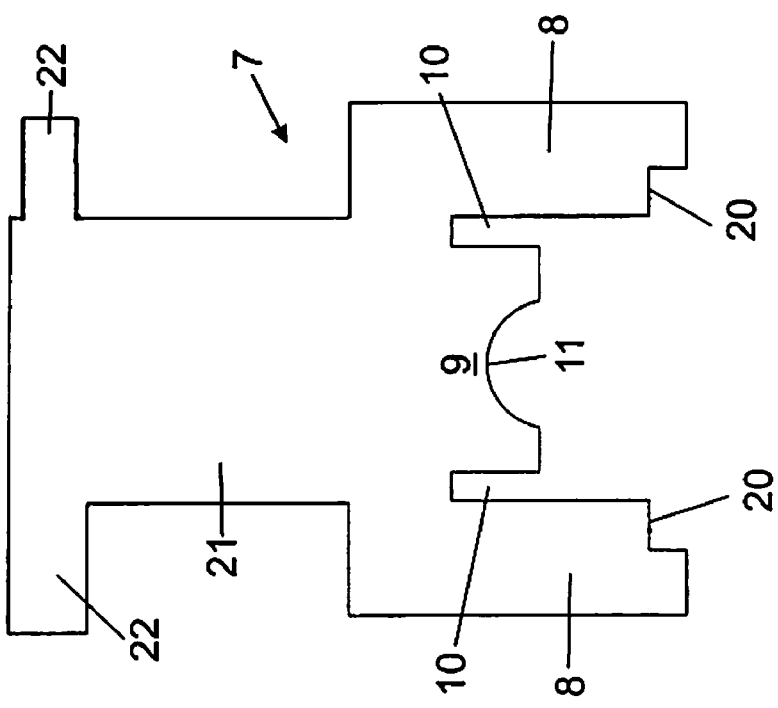
FIGS. 7a and 7b show developed views of the closing springs of the brackets of FIGS. 6a and 6b.
Figure 7B:
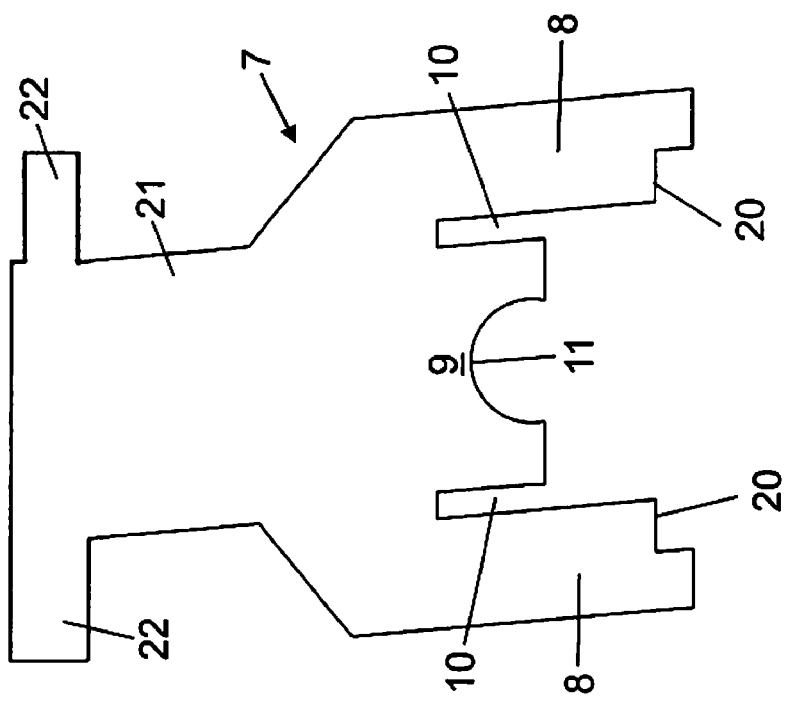

FIGS. 7a and 7b show developed views of closing springs 7 belonging to the brackets of FIGS. 6a and 6b. It is possible to see clearly here reduced-width section 21, which is intended to form the arc; laterally projecting tabs 22, which are formed on the end of the arc and which are intended to form the pivot bearings; and centering sections 20 on the free ends of ligating tongues 8.

FIGS. 8a-8c and FIG. 9 show a second embodiment of the invention, in which one ligating tongue 8 is formed on closing spring 7 between two latching tongues 9, the tongues being separated from each other by notches 10. Devices with an undercut 12 are provided on second tie wing 4b of upper bracket structure 4. Such devices hold free ends 25 of latching tongues 9 in the closed position of closing spring 7. These devices are formed by a projection 13, which is formed on second tie wing 4b and lies on the other side of slot 5 provided in upper bracket structure 4 to receive an arch wire 6. In the example shown here, ligating tongue 8 is shorter than latching tongues 9, so that ligating tongue 8 is able to fit into slot 5 when closing spring 7 is closed. So that the ligating tongue can assume this position, at least first tie wing 4a of upper bracket structure 4 must comprise a gap extending transversely to the longitudinal direction of slot 5. If this gap also extends into second tie wing 4b, ligating tongue 8 does not have to be shortened.

A bracket of this type can therefore be used as an active bracket, as already described above.

FIGS. 8a-8c show the second embodiment of the invention with closing spring 7 in various states. FIG. 8a shows the completely opened position, in which slot 5 has been completely opened for the insertion or removal of an arch wire 6. Arc 21 of closing spring 7 adjacent to first spring end 22 is under pre-tension, which tries to curve the arc inward. This pre-tension is able to clamp closing spring 7 frictionally to first tie wing 4a, so that closing spring 7 is held in the opened state shown in FIG. 8a without the need for any further measures.

FIGS. 8a and 8b, show transition states during the closing of closing spring 7. As can be seen, closing spring is curved in such a way during its fabrication that, in the resting state of tongues 8 and 9 of closing spring 7, ligating tongue 9 projects farther than latching tongues 8 toward slot 6. This has the result that, when closing spring 7 is in the completely closed state shown in FIG. 8c, ligating tongue 9 rests with pretension on arch wire 6 lying in slot 5 and thus presses it down onto the base of the slot. Free ends 25 of latching tongues 8 lie under undercut 12 on projection 13 on second tie wing 4b and are supported thereon, thus holding closing spring 7 in position against the force of reaction originating from ligating tongue 9.

As will be understood, when second tie wing 4b is divided by a gap, the two sections of second tie wing 4b at the sides of the gap are each provided with a projection 13 and an undercut 12. Such construction is best shown in the embodiment illustrated in FIGS. 1 and 2, but is similar in that of FIGS. 8 and 9.

Figure 9:
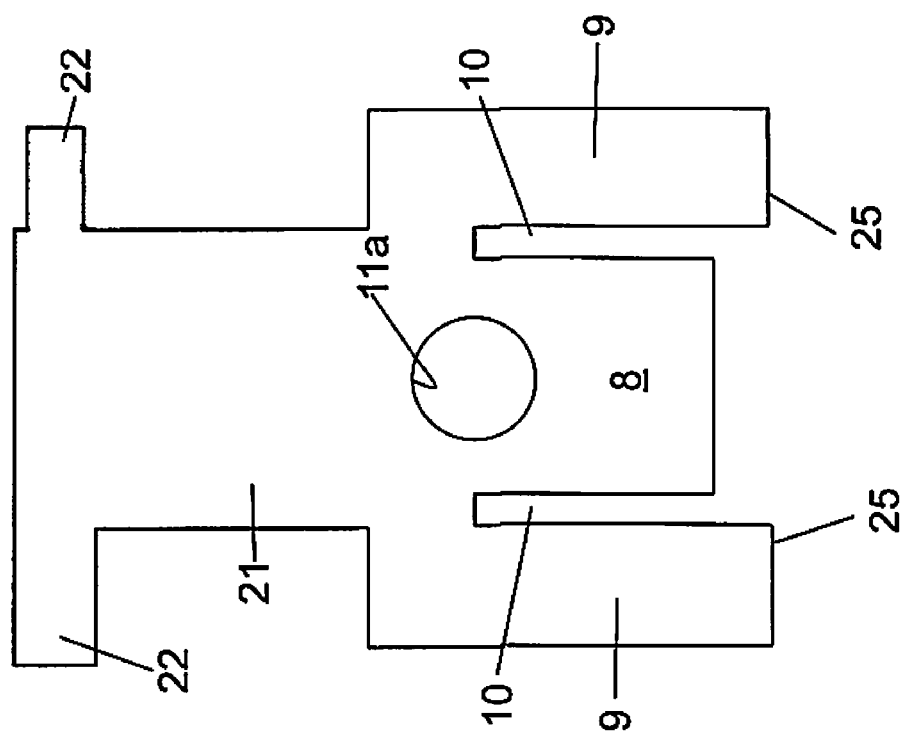
FIG. 9 illustrates the developed state of the closing spring of the brackets of FIGS. 8a-8c.

FIG. 9 shows a developed view, from above, of closing spring 7 of the embodiment according to FIGS. 8a-8c. It is possible to see the different lengths of latching tongues 9 and ligating tongue 8. A hole 11a can also be seen in the root area of ligating tongue 8. This serves to accept a needle-like tool (not shown), which the orthodontist uses when he wants to open and close closing spring 7.

The other features of this embodiment are the same as those which have already been described on the basis of the example according to FIGS. 1-7b, for which reason there is no need to explain these features again here.

It should also be noted that the second embodiment of the invention can also be modified in such a way that only one latching tongue is provided, which is framed laterally by two ligating tongues. In this case, the ligating tongues can be pushed up elastically, individually and to different degrees, by an arch wire lying in the slot when, e.g., the arch wire is not resting flat over its entire length on the base of the groove but is rather elevated on one side in correspondence with the malposition of the tooth to be corrected. On the basis of the explanation of FIGS. 8a-9 above, those of ordinary skill in the art will fully understand how the upper bracket structure will have to be adapted to accommodate such operation and, as such, these modifications have not been specifically illustrated herein.

FIGS. 10-16c illustrate other highly preferred embodiments of this invention, each involving a form of the tabs for engagement of closing spring 7 with upper structure 4 which are referred to herein as "torsion tabs" because of how they are used to secure closing spring 7 to upper structure 4. Torsion tabs 22s differ from tabs 22 as referred to above in their nature and how they are used, which will hereafter be described in detail. As in certain of the above-described embodiments, during the assembly process torsion tab 22a of closing spring 7 is guided into bore 15 through feed slot 16, and it is possible in principle to remove closing spring 7 by guiding torsion tab 22a back out of feed slot 16.

Figure 11:
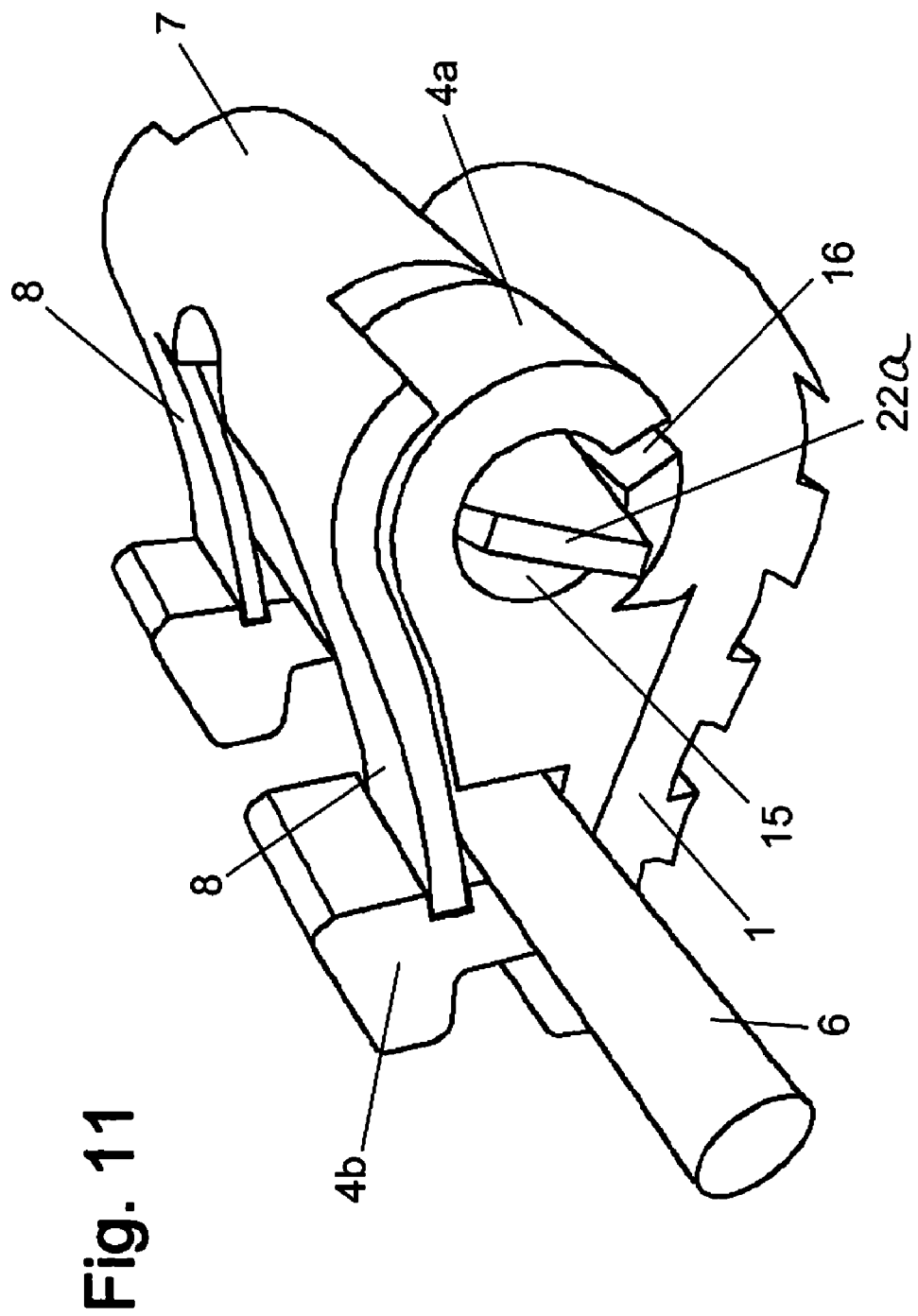
FIG. 11 is a perspective view of the device of FIG. 10, but with the closing spring having been secured by twisting of the torsion tab.

However, to prevent this, torsion tab 22s, as shown in FIG. 11, is twisted around its torsion axis by means of a tool, such as a suitable pair of pliers, so that the downward-facing edge of torsion tab 22a at the free end is moved a certain distance away from feed slot 16. In this deformed position, it is now impossible to introduce torsion tab 22a into feed slot 16. This effectively prevents closing spring 7 from falling out of the upper structure of the bracket or from being removed from it. The securing function, however, is reversible. The pliers mentioned above can be used to deform the free end of torsion tab 22a again, i.e., to twist it back in such a way that closing spring 7 can be slid back out through feed slot 16 again.

Figure 10:
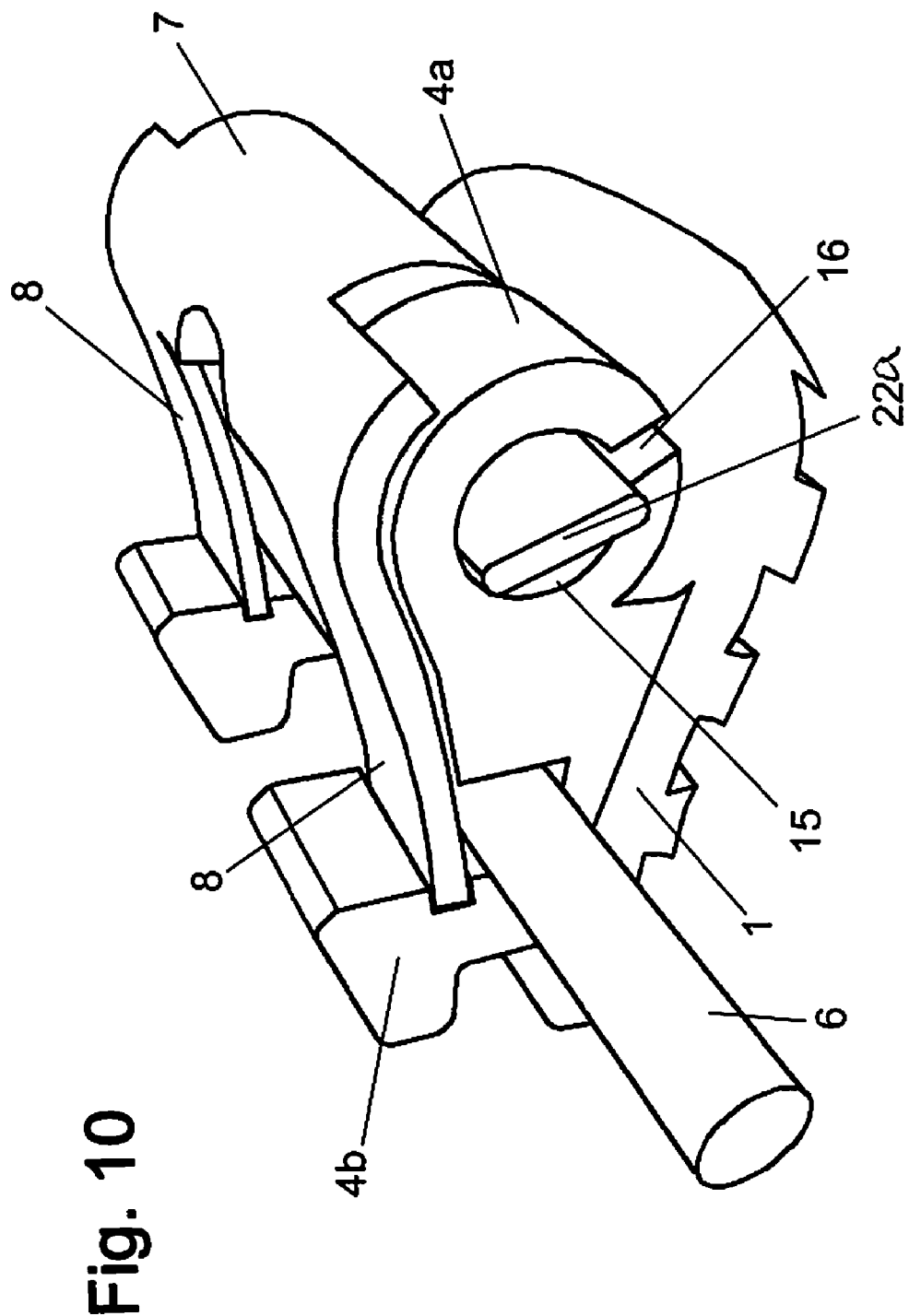
FIG. 10 is a perspective view of another embodiment of the bracket of this invention, with the closing spring has not yet been secured.

It should be noted that, in both of the states shown in FIGS. 10 and 11, the closing spring is free to rotate inside bore 15, so that, in the manner of a hinge, closing spring 7 can be opened or closed to allow insertion or removal of arch wire 6. The dimensions of torsion tab 22a and of bore 15 are adapted to each other in such a way that both the twisting and the reverse twisting as well as the hinge function all remain possible.

Figure 12:
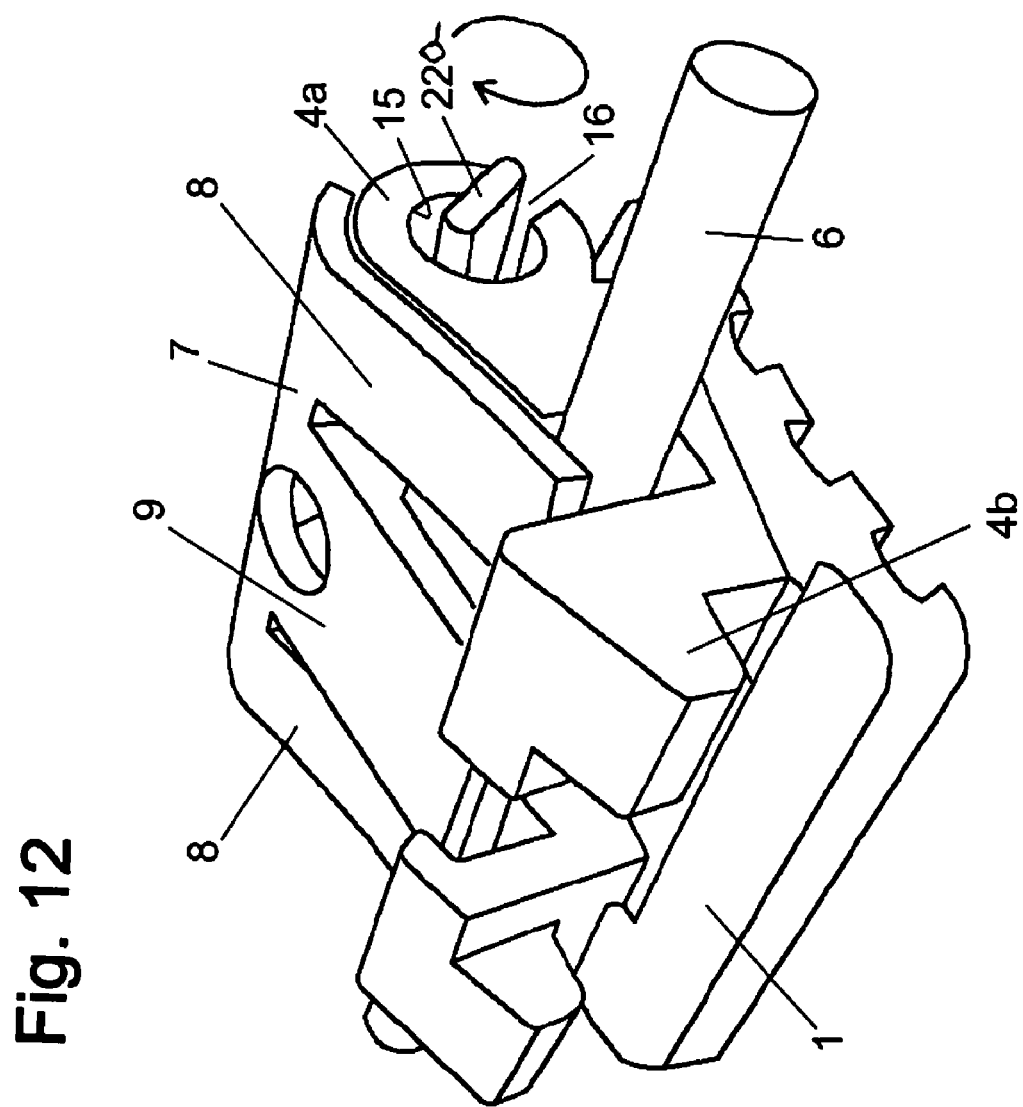
FIG. 12 is a perspective view of a yet another embodiment of an inventive bracket, with the closing spring has not yet been secured.
Figure 13:
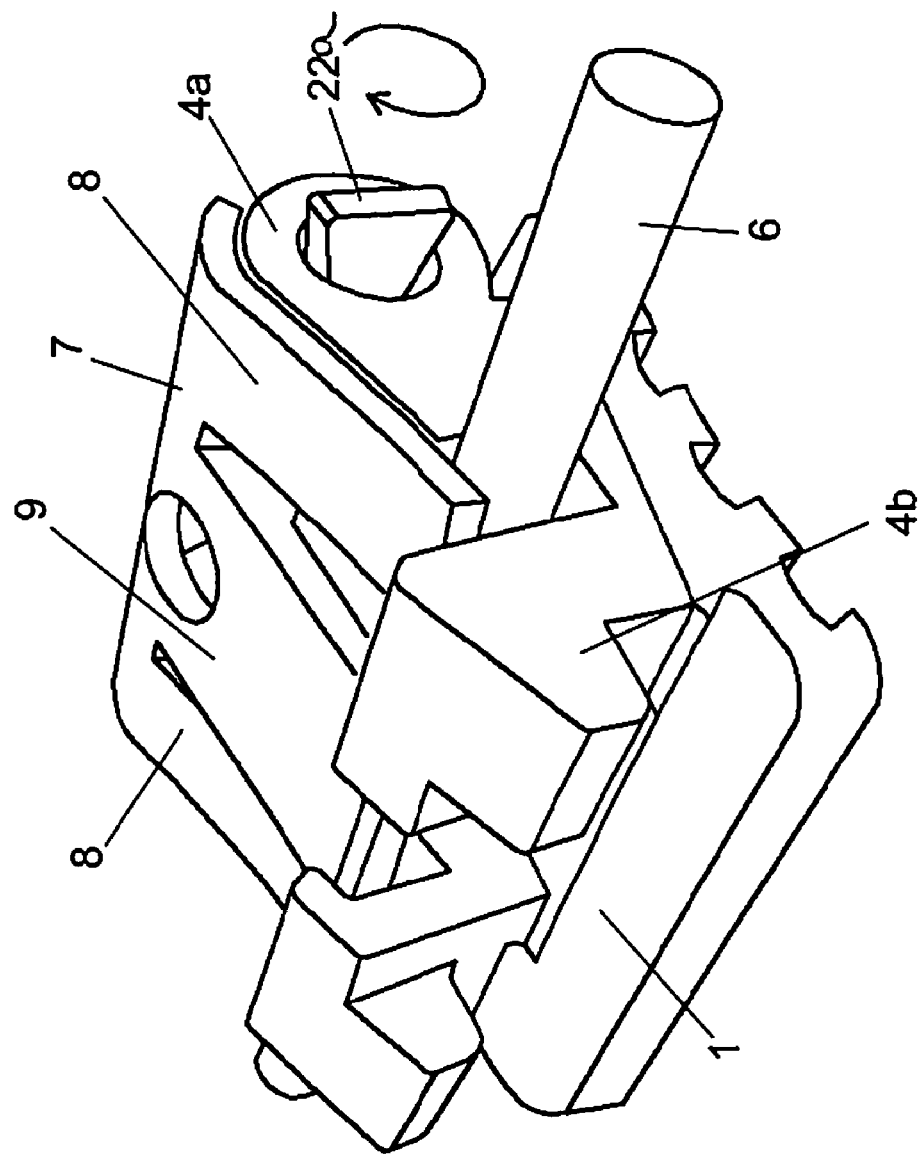
FIG. 13 is a perspective view of the embodiment of FIG. 12, but with the closing spring having been secured by twisting its torsion tab.

FIGS. 12 and 13 show perspective views of another embodiment of the inventive bracket with a closing spring lock. An active bracket is shown, in which locking tongue 9 is longer than ligating tongues 8, which, when closing spring 7 is in the closed state, exert a force on arch wire 6 but do not project beyond slot 5. The closing spring is locked by the engagement of locking tongue 9 with the two half-sections of second wing 4b of the upper structure. As previously in FIGS. 10 and 11, we see torsion tab 22a in bore 15, projecting here slightly beyond the edge of first wing 4a. This tab is turned clockwise around its torsion axis from the position shown in FIG. 12, which results in the arrangement shown in FIG. 13.

Figure 14B:
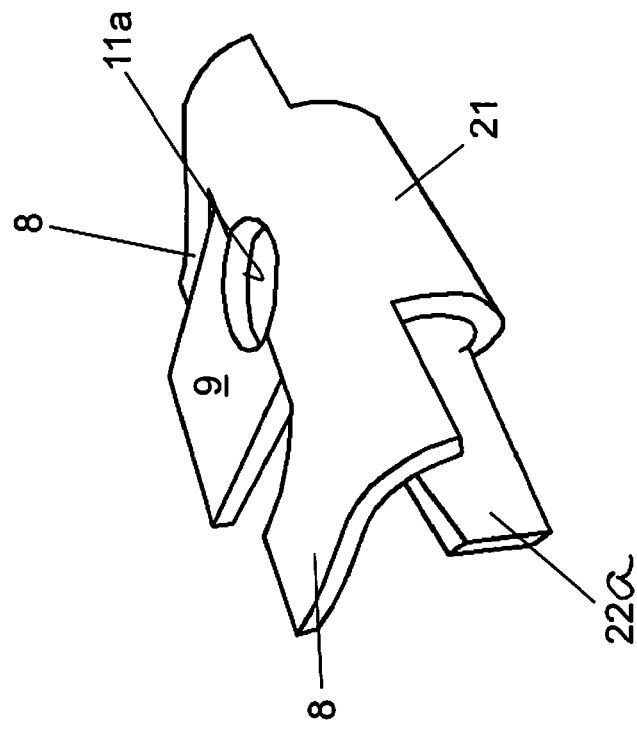
FIGS. 14a and 14b are perspective views of the closing springs of the brackets of FIGS. 12 and 13, but without the upper structure.
Figure 14A:
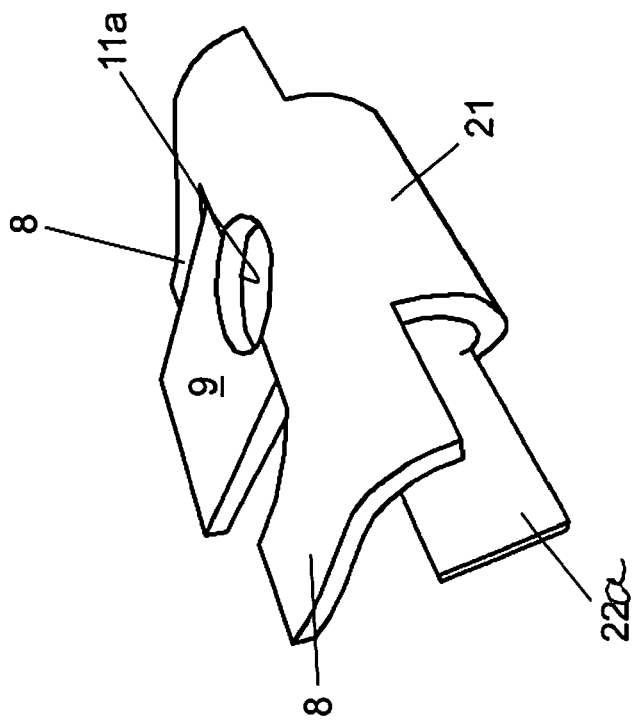

FIGS. 14a and 14b show perspective views of the closing springs belonging to the brackets of FIGS. 12 and 13. In addition to locking tongues 9 and ligating tongues 8, we see recess 11a, into which the closing tool fits. The reduced-width section 21 connects locking tongue 9 and ligating tongues 8 to torsion tab 22a, the length of which can be varied as required. FIG. 14a shows torsion tab 22a in the undeformed insertion-and-removal state; FIG. 14b shows torsion tab 22a in the deformed state.

FIGS. 15a and 15b show developed views of two examples of closing springs 7. We can clearly see here, too, the reduced-width section 21 which is intended to form the curved section, and the laterally projecting torsion tabs 22 which are formed on the end of the reduced-width section and are intended to serve as the pivot bearings. In FIG. 15b, a vertically shaded projecting area 230 is shown which makes torsion tab 22a longer than the closing spring shown in FIG. 15a. Additional details have already been described thoroughly above, which means that there is no need to explain them again here.

Figure 16A:
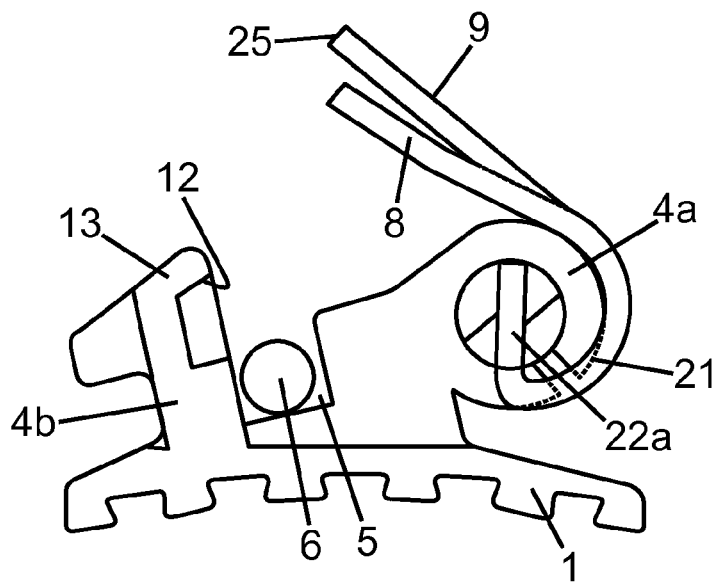
FIGS. 16a-16c are side views of the bracket of FIGS. 12 and 13 with the closing spring in various positions.
Figure 16B:
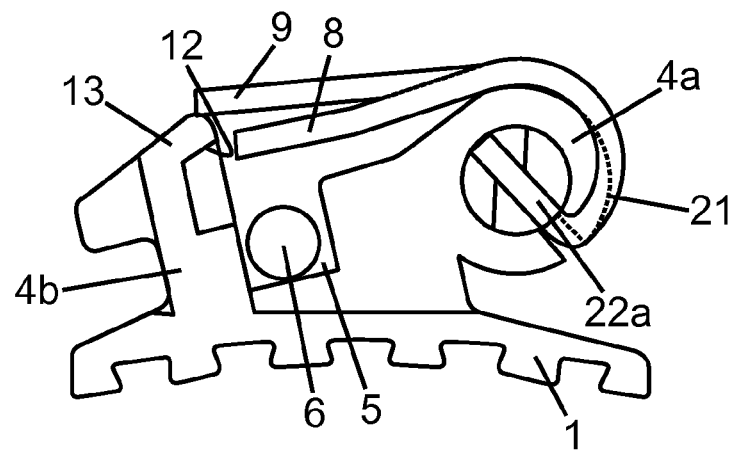
Figure 16C:
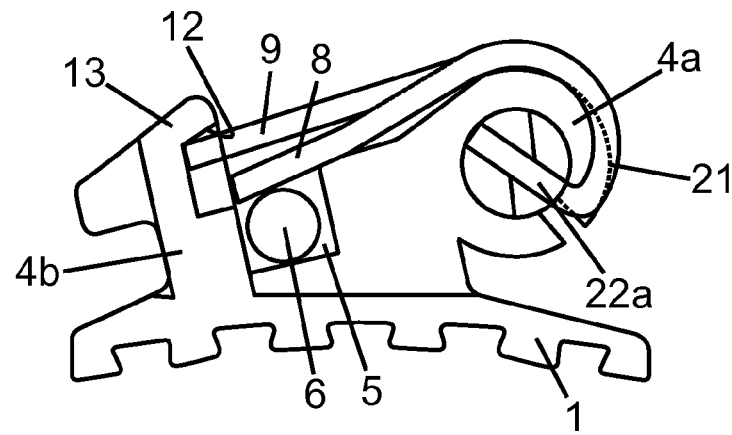

FIGS. 16a-16c show another embodiment of the invention with the closing spring 7 in various states. FIG. 16a shows the bracket from the side in the completely opened state of closing spring 7. It can be seen that closing spring 7 has been pivoted into a completely opened end position in the hinge formed by bore 15 in cooperation with torsion tab 22a. A ligating tongue 8 is formed on closing spring 7 between two locking tongues 9, wherein locking tongues 9 are separated from each other by notches 10 (see FIGS. 15a and 15b). On second wing 4b of upper bracket structure 4, devices with an undercut 12 are provided, which have the purpose of capturing free ends 25 of locking tongues 9 in the closed position of closing spring 7. These devices are formed by a projection 13, which is formed on second wing 4b and lies on the other side of slot 5 provided to hold an arch wire 6 in bracket structure 4. In the example shown here, ligating tongue 8 is shorter than locking tongues 9, so that ligating tongue 8 is able to dip into slot 5 when closing spring 7 is closed. This dipping action is possible provided that at least first wing 4a of bracket structure 4 includes a gap which extends transversely to the longitudinal dimension of slot 5. If this gap also extends into second wing 4b, ligating tongue 9 does not need to be shortened. A bracket of this type can be used as an active bracket, as previously described, because the ligating tongue acts on the arch wire without being locked or held in place by second wing 4b.

While the principles of the invention have been shown and described in connection with specific embodiments, it is to be understood that such embodiments are by way of example and are not limiting.

The invention claimed is:

1. A self-ligating orthodontic bracket comprising:
   a base member having a base plate with a bottom side adapted to be attached to a tooth and a top side from which upper structure extends upwardly, the upper structure having first and second tie wings between which there is an arch-wire-receiving slot, the first tie wing having at least one bore radially accessible by a feed slot; and a closing spring member having a first end which is anchored to the first tie wing and a second end which is movable between an opened position in which the slot arch-wire-receiving slot is freely accessible for the insertion of the archwire and a closed position, the closing spring member having has a torsion tab dimensioned to be introduced into the bore through the feed slot, the torsion tab being deformable by twisting at its free end into a changed shape in such a way that it cannot be removed and fall out of such bore until it is twisted back into its original shape.

2. The self-ligating orthodontic bracket of claim 1 wherein the angle by which the torsion tab can be twisted is within the range of about 5-60°.

3. The self-ligating orthodontic bracket of claim 2 wherein the angle by which the torsion tab can be twisted is within the range of about 10-30°.

4. The self-ligating orthodontic bracket of claim 1 comprising a pair of such bores and a pair of such torsion tabs, each insertable in a respective one of the bores.

5. The self-ligating orthodontic bracket of claim 1 wherein the torsion tab comprises a bearing such that the free end of the torsion tab can twist substantially around the axis of the bore with respect to the other end of the torsion tab.

6. The self-ligating orthodontic bracket of claim 1 wherein the bracket is designed as a passive bracket, the closing spring member having a second end with retaining elements by which the spring member secures the arch wire in the arch-wire-receiving slot.

7. The self-ligating orthodontic bracket of claim 1 wherein the bracket is designed as an active bracket, the closing spring member having a second end with retaining elements by which the spring member secures the arch wire in the arch-wire-receiving slot and simultaneously can exert torque thereon.

* * * * *

UNITED STATES PATENT AND TRADEMARK OFFICE
CERTIFICATE OF CORRECTION

| | | |
|---|---|---|
| PATENT NO. | : 8,246,348 B2 | Page 1 of 1 |
| APPLICATION NO. | : 12/828917 | |
| DATED | : August 21, 2012 | |
| INVENTOR(S) | : Heiser | |

It is certified that error appears in the above-identified patent and that said Letters Patent is hereby corrected as shown below:

On the Title Page
    Item (76) Inventor: Wolfgang Heiser, Innsbruck delete "(AU)" and insert --(AT)--.

Signed and Sealed this
Twenty-eighth Day of May, 2013

Teresa Stanek Rea
*Acting Director of the United States Patent and Trademark Office*